(12) United States Patent
Ueda

(10) Patent No.: US 9,713,654 B2
(45) Date of Patent: Jul. 25, 2017

(54) BONE CEMENT COMPOSITION

(71) Applicants: Ishihara Sangyo Kaisha, Ltd., Osaka (JP); Kyoto University, Kyoto (JP)

(72) Inventor: Yoshimichi Ueda, Kusatsu (JP)

(73) Assignees: ISHIHARA SANGYO KAISHA, LTD., Osaka (JP); KYOTO UNIVERSITY, Kyoto (JP)

( * ) Notice: Subject to any disclaimer, the term of this patent is extended or adjusted under 35 U.S.C. 154(b) by 343 days.

(21) Appl. No.: 14/381,922

(22) PCT Filed: Feb. 25, 2013

(86) PCT No.: PCT/JP2013/054711
§ 371 (c)(1),
(2) Date: Aug. 28, 2014

(87) PCT Pub. No.: WO2013/129292
PCT Pub. Date: Sep. 6, 2013

(65) Prior Publication Data
US 2015/0056289 A1    Feb. 26, 2015

(30) Foreign Application Priority Data

Feb. 29, 2012 (JP) ................. 2012-043418
Aug. 21, 2012 (JP) ................. 2012-182252

(51) Int. Cl.
A61K 9/16       (2006.01)
A61L 24/00      (2006.01)
A61L 27/44      (2006.01)
A61L 27/50      (2006.01)
A61L 24/06      (2006.01)

(52) U.S. Cl.
CPC ......... *A61L 24/001* (2013.01); *A61L 24/0089* (2013.01); *A61L 27/446* (2013.01); *A61L 27/50* (2013.01); *A61L 2430/02* (2013.01)

(58) Field of Classification Search
CPC ...... A61L 24/001; A61L 27/446; A61L 27/50; A61L 24/0089
See application file for complete search history.

(56) References Cited

U.S. PATENT DOCUMENTS

| 8,609,746 B2 | 12/2013 | Nakamura et al. |
| 2009/0187253 A1 | 7/2009 | Astrand et al. |
| 2012/0046385 A1* | 2/2012 | Nakamura .......... A61L 24/0089 523/116 |

FOREIGN PATENT DOCUMENTS

| JP | 2004-201869 | 7/2004 |
| JP | 2007-54619  | 3/2007 |
| JP | 2011-514818 | 5/2011 |
| JP | 2012-40213  | 3/2012 |
| WO | WO 2009-108893 | 9/2009 |
| WO | WO 2009/108893 | 9/2009 |
| WO | WO 2010-098305 | 9/2010 |

* cited by examiner

*Primary Examiner* — Nannette Holloman
(74) *Attorney, Agent, or Firm* — Paul E. White, Jr.; Manelli Selter PLLC

(57) ABSTRACT

The purpose of the present invention is to provide a bone cement composition which can have desired biological activity performance and desired radiolucency while enabling the strength of a cured product thereof to be kept. A titanium oxide coating is formed on radiolucent particles to thereby produce composite particles, and the composite particles are added to a bone cement composition. The bone cement composition thus produced can be used suitably for the filling of a bone defect portion and the fixation of an artificial joint and in percutaneous vertebroplasty. The shape of each of the radiolucent particles is preferably granular, and the titanium oxide is preferably of a rutile type.

12 Claims, 7 Drawing Sheets

COMPOSITE PARTICLE 10%

BaSO₄ 30%

100 μm

COMPOSITE PARTICLE 20%

COMPOSITE PARTICLE 30%

6μm

COMPOSITE PARTICLE 10%

COMPOSITE PARTICLE 20%

BONE CEMENT COMPOSITION

TECHNICAL FIELD

The present invention relates to a bone cement composition. More specifically, it relates to a bone cement composition, a bone cement composition kit, a method for producing the bone cement composition, and a hardened product of the bone cement composition.

BACKGROUND ART

A polymethyl methacrylate (PMMA) bone cement composition is widely used as a prosthetic material for a bone defective part, as an adhesive for fixing a metallic prosthesis such as a hip prosthesis to its surrounding bones, or the like. An existing PMMA cement composition containing a contrast agent such as barium sulfate or zirconium dioxide, however, does not have bioactivity, namely, bone bonding performance, and thus causes the following problem: loosening between a bone cement and the bone due to the course of a long period after application. In order to solve such a problem, there has been proposed a bone cement composition to which titanium dioxide particles are added for the purpose of imparting bioactivity (JP 2007-54619 A).

In recent years, vertebroplasty has been used as a fast-acting therapeutic method for alleviating pain due to compression fracture associated with metastasis of malignant tumors to the vertebral body or associated with osteoporosis. This method is a method for injecting a bone cement to a damaged portion of the vertebral body to reinforce the vertebral body. Since a fluid bone cement is directly injected into the vertebral body, the bone cement may be leaked from the damaged portion and the like to the outside of the vertebral body. Therefore, it is necessary to add to a bone cement a predetermined amount of an inorganic compound having radiopacity, such as barium sulfate particles or zirconium dioxide particles, and to make procedure, while an image obtained by an X-ray inspection apparatus being observed, so that the bone cement is not leaked (JP 2011-514818 A).

CITATION LIST

Patent Literatures

Patent Literature 1: JP 2007-54619 A
Patent Literature 2: JP 2011-514818 A

SUMMARY OF INVENTION

Technical Problem

As described above, it is known to allow a bone cement composition to include a predetermined amount of titanium dioxide particles in order to impart bioactivity to the bone cement composition, and it is also known to allow a bone cement composition to include a predetermined amount of an inorganic compound such as barium sulfate particles or zirconium dioxide particles in order to impart radiopacity to the bone cement composition.

When a predetermined amount of titanium dioxide particles are added in order to impart the desired bioactivity, and furthermore a predetermined amount of barium sulfate particles or zirconium dioxide particles are also added in order to afford the desired radiopacity (hereinafter, particles to be added for these purposes may be simply collectively referred to as "filler"), however, the content rate of the filler in the bone cement composition is high and the strength of the resulting hardened product is necessarily reduced.

In addition, when such a filler is used with being simply added and mixed, it easily aggregates, causing the reduction in strength of the hardened product.

Solution to Problem

The present inventors have intensive studies in order to solve the above problems, and as a result, have found that a bone cement composition is allowed to include a composite particle in which titanium dioxide coating is formed on a particle having radiopacity, to thereby achieve the desired bioactivity and the desired radiopacity while the strength of a hardened product is maintained, completing the present invention.

That is, the present invention relates to a bone cement composition comprising (a) a composite particle comprising a particle having radiopacity and a titanium dioxide coating with which the particle having radiopacity is coated, and (b) a base material formation component comprising a methacrylate polymer.

Preferably, the particle having radiopacity has a granular shape, the composite particle has a median diameter of 0.2 to 7 μm and a BET specific surface area of 1 to 30 m²/g, the titanium dioxide coating is rutile titanium dioxide, the composite particle further comprises a silica coating, and the particle having radiopacity is barium sulfate or zirconium dioxide.

The present invention also relates to a bone cement composition kit comprising a first component comprising a polymerization initiator and a second component comprising a methacrylate monomer, wherein the first component and/or the second component comprise(s) the above composite particle. The methacrylate monomer in the kit can be polymerized to thereby provide a bone cement composition, and the bone cement composition can be hardened to provide a hardened product.

Advantageous Effects of Invention

The bone cement composition using a composite particle in which a titanium dioxide coating is formed on a particle having radiopacity, of the invention of the present application, is suitably used for filling in a bone defective part, for fixing of a prosthesis, and for vertebroplasty. The bone cement composition of the invention of the present application can exert the desired bioactivity and the desired radiopacity while the strength of the hardened product is maintained.

DESCRIPTION OF EMBODIMENTS

Figure 1:
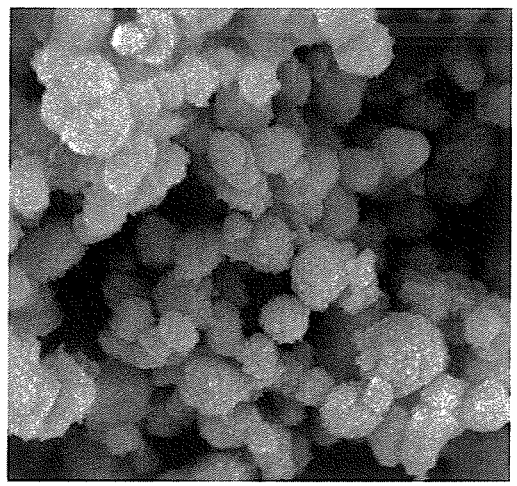
FIG. 1 is a scanning electron micrograph (SEM) of composite particles by a simultaneous neutralization method.

The bone cement composition of the present invention is characterized by containing (a) a composite particle comprising a particle having radiopacity and a titanium dioxide coating with which the particle having radiopacity is coated, and (b) a base material formation component comprising a polymethacrylate polymer.

(Particle Having Radiopacity)

The particle having radiopacity (hereinafter, sometimes simply referred to as a "particle") includes a particle of barium sulfate or zirconium dioxide.

The shape of the particle may be any shape as long as the shape can be obtained by a usual industrial production method, and not only irregular shape particles but also particles having any of various known shapes such as granular, spherical, plate, flake, needle, rod, fiber and columnar shapes can also be used. The shape is preferably granular and more preferably spherical in terms of the physical strength of the resulting hardened product of the bone cement composition. A shape having an aspect ratio (value obtained by dividing the average long diameter by the average short diameter) of 1 to 1.6 is referred to as being granular, and a shape having an aspect ratio of 1 to 1.3 is referred to as being spherical.

The particle preferably has a median diameter measured by a laser diffraction/scattering-type particle size distribution analyzer (the same shall apply hereinafter) of 0.2 to 7 μm, more preferably 1.5 to 7 μm, further preferably 2 to 5 μm, and particularly preferably 2 to 4 μm. As the laser diffraction/scattering-type particle size distribution analyzer, for example, a particle size distribution measurement apparatus "LA-950" (manufactured by Horiba Ltd.) can be used.

When the median diameter of the particle is excessively small, the physical strength (for example, bending strength) of the resulting hardened product of the bone cement composition is easily low. On the other hand, when the median diameter of the particle is excessively large, the physical strength (for example, bending strength) of the resulting hardened product of the bone cement composition is excessively high, easily causing the following drawback: bone fracture easily occurs due to a large difference in physical strength between the hardened product and the bone of a portion to which the hardened product is applied, for example.

In addition, the particle preferably has a BET specific surface area measured by a nitrogen adsorption method (the same shall apply hereinafter) of 1 to 30 $m^2/g$, further preferably 1 to 10 $m^2/g$, and particularly preferably 1 to 5 $m^2/g$. The BET specific surface area by a nitrogen adsorption method can be measured using, for example, a BET specific surface area measurement apparatus "MONOSORB" (manufactured by Quantachrome Instruments).

When the BET specific surface area of the particle is excessively small, the median diameter is large, and as a result, the physical strength (for example, bending strength) of the resulting hardened product of the bone cement composition is excessively high, thereby often causing the following drawback: bone fracture easily occurs due to a large difference in physical strength between the hardened product and the bone of a portion to which the hardened product is applied, for example. On the other hand, when the BET specific surface area of the particle is excessively large, the median diameter is excessively small, or a porous state is caused, thereby often not providing a physical strength (for example, bending strength) practically required for the resulting hardened product of the bone cement composition.

In addition, when the BET specific surface area of the particle is 1 to 30 $m^2/g$, the particle can be a dense particle having the desired median diameter (median diameter suitable for the bone cement composition), thereby allowing the resulting hardened product of the bone cement composition to have a physical strength (for example, bending strength) practically required therefor.

The particle may be coated with or adsorb to an inorganic compound or an organic compound before being coated with titanium dioxide. The inorganic compound includes, in addition to $TiO_2$ having a different crystal form from that of the titanium dioxide for coating, $SiO_2$, $Al_2O_3$, $ZrO_2$, $SnO_2$, $Fe_2O_3$, $Fe_3O_4$ and calcium phosphate. The organic compound includes a polycarboxylic acid, a polyacrylic acid, a sulfonic acid, a phosphoric acid or nonionic surfactant, a silane coupling agent and silicone.

(Titanium Dioxide Coating)

The composite particle of the present invention has a titanium dioxide coating with which the particle is coated. The titanium dioxide coating with which the particle is coated means a titanium dioxide coating with which the surface of the particle is partially or entirely coated directly or via another layer.

The crystal form of the titanium dioxide may be rutile or anatase, or a mixed phase of anatase and rutile, but is preferably rutile excellent in apatite formation ability in terms of the physical strength of the resulting hardened product of the bone cement composition.

In addition, in order to exert good bioactivity, the titanium dioxide coating is preferably present on the particle without being ununiformly located.

The titanium dioxide coating is present on a part or the entire of the surface of the particle, and the coating rate is preferably 50 to 100% in order to exert good bioactivity. The coating rate here means the rate of the titanium dioxide coating present on the entire surface of the composite particle. The coating rate can be determined by using an image processing software WinROOF (manufactured by Mitani Corporation) to calculate the area of a part, in which the titanium dioxide coating is not present on the surface of the composite particle, in the image of the surface of the composite particle observed by a scanning electron microscope.

In order to exert good bioactivity, preferably, the amount of coating of the titanium dioxide is 1 to 30% by weight relative to the amount of the composite particle, and the coating thickness is 1 to 2000 nm. The coating rate of the titanium dioxide, the amount thereof for coating and the coating thickness can be appropriately adjusted experimentally by the ratio of titanium loaded to the particle. The titanium dioxide coating may contain a different element from titanium within the crystal lattice thereof being, if necessary, doped with the element, for example.

(Composite Particle)

The shape of the composite particle depends on the shape of the particle having radiopacity, and is preferably granular and more preferably spherical. The diameter thereof also depends on the diameter of the particle having radiopacity, the median diameter is preferably 0.2 to 7 µm, more preferably 1.5 to 7 µm, further preferably 2 to 5 µm and particularly preferably 2 to 4 µm, and the BET specific surface area is preferably 1 to 30 m$^2$/g, further preferably 1 to 10 m$^2$/g and particularly preferably 1 to 5 m$^2$/g.

The surface of the composite particle may be, if necessary, coated with at least one selected from an inorganic compound such as carbon, silica or alumina, and an organic compound such as a surfactant or a coupling agent. When two or more are used, each can be coated one layer by one layer, or a mixture or a composite of two or more can be coated as one layer. A coating method is not particularly limited, and a known method can be used. In order to more effectively exert bioactivity, the titanium dioxide coating is preferably exposed.

(Method for Producing Composite Particle)

The composite particle can be produced by a simultaneous neutralization method, a spray coating method, a mechanical dry-treatment method, or the like.

The simultaneous neutralization method is a method including a step of depositing titanium dioxide on the surface of the particles having radiopacity with the pH being kept at 1 to 3 in the presence of an α-hydroxycarboxylic acid. According to this method, the titanium dioxide coating can be formed even on granular or spherical particles without being ununiformly located.

Specifically, an α-hydroxycarboxylic acid and water are added to, for example, a slurry of granular barium sulfate serving as a nucleus and heated to 50 to 100° C., and the pH is adjusted to 1 to 3. To this slurry, water in which a titanium compound is dissolved, and an aqueous solution containing a hydroxide of an alkali metal, a carbonate of an alkali metal, or ammonia are slowly added dropwise with the pH being kept at 1 to 3, thereby providing composite articles in which titanium dioxide is precipitated on the surface of barium sulfate. The resulting composite particles are separated, dried, and, if desired, calcined at a temperature of 400 to 1000° C. Titanium dioxide has been difficult to precipitate on the surface of particles without being ununiformly located, but this method makes it possible to precipitate titanium dioxide on the surface of the particles without titanium dioxide being ununiformly located.

In addition, barium sulfate has such directionality as to allow titanium dioxide to be precipitated as an anatase crystal, but this method makes it possible to precipitate rutile titanium dioxide.

As the α-hydroxycarboxylic acid, for example, glycolic acid, lactic acid, citric acid, tartaric acid, salicylic acid, benzilic acid, mandelic acid, hydroxysuccinic acid, oxalic acid, and salts thereof can be used. The amount of the α-hydroxycarboxylic acid used is in a range from 0.1 to 0.9 in a molar ratio based on titanium, and in such a range as to allow rutile titanium dioxide to be precipitated. When the amount of the α-hydroxycarboxylic acid used is excessive, anatase titanium dioxide is precipitated.

The titanium compound is not particularly limited as long as it forms titanium dioxide by a chemical reaction, and examples include titanium tetrachloride, titanium oxychloride, titanium nitrate and titanium alkoxide.

Examples of the hydroxide of an alkali metal include sodium hydroxide and potassium hydroxide, and examples of the carbonate of an alkali metal include sodium carbonate and potassium carbonate.

The concentration of the slurry of barium sulfate, the reaction temperature and the reaction time in neutralization, the calcining temperature and the calcining time in calcining, and the like are appropriately set experimentally.

In the spray coating method, an apparatus for coating includes general fluid bed granulators (tambling fluid bed granulator, Wurster fluid bed granulator, and the like), but is preferably a complex fluid bed granulator forced circulation apparatus (MP-01SFP manufactured by Powrex Corp., and the like) equipped with a sizing and pulverizing mechanism (screen-impeller system, blade stator system, and the like). Such an apparatus can be used to spray a slurry of titanium dioxide having the desired crystal form to the particles having radiopacity, thereby producing the composite particles.

The production method by the mechanical dry-treatment method is a method in which the particles having radiopacity and the titanium dioxide for coating are mixed and mechanical energy is applied thereto for mechanochemical composition, thereby producing the composite particles. In the mechanical dry-treatment method, for example, a high-speed impact-type dry powder composition apparatus (Hybridization system manufactured by Nara Machinery Co., Ltd.), a compression shearing-type dry powder composition apparatus (Theta Composer manufactured by Tokuju Co., Ltd., Mechano Micros manufactured by Nara Machinery Co., Ltd., Mechanofusion System manufactured by Hosokawa Micron, Nobilta manufactured by Hosokawa Micron), or the like can be used.

The production of the composite particles by the mechanical dry-treatment method can be performed by using such an apparatus to mechanically mixing the particles having radiopacity and titanium dioxide particles having the desired crystal form. The mixing ratio of the particles having radiopacity to the titanium dioxide particles may be adjusted to any ratio, the mixture may be charged to a dry composition apparatus and pre-mixed for a certain time without compression shearing energy being loaded thereto, and thereafter the energy is loaded thereto for coating with titanium dioxide. Alternatively, the particles having radiopacity and the titanium dioxide particles may be mixed in advance by a mixing machine such as a Henschel mixer, and thereafter charged to a dry composition apparatus for coating with titanium dioxide. Coating conditions are not particularly limited, and may be appropriately selected depending on, in addition to the specification and the setting of the apparatus used, the mixing ratio of the particles having radiopacity to the titanium dioxide particles, the treatment time, the treatment temperature, and the like. In addition, appropriately, calcining may be made in order to fix the titanium dioxide subjected to coating, and a pulverization treatment may be made after calcining.

When the composite particles are produced by the mechanical dry-treatment method, the particle diameter of the particles having radiopacity is preferably in a range from 10 times to 2000 times and further preferably in a range from 50 times to 1000 times relative to the particle diameter of the titanium dioxide particles for coating because the surface of the particles having radiopacity is required to be coated with titanium dioxide to be held.

A specific particle diameter of the particles having radiopacity is the same as described above, but the particle diameter of the titanium dioxide particles is essentially at least smaller than that of the particles having radiopacity because the surface of the particles having radiopacity is required to be coated. A specific particle diameter of the titanium dioxide particles is preferably in a range from 1 nm to 100 nm, more preferably in a range from 10 nm to 100 nm and further preferably in a range from 10 nm to 50 nm. If the particle diameter is less than 1 nm, the particles easily aggregate, and if it is more than 100 nm, the surface of the particles having radiopacity is hardly coated.

The amount of coating of the titanium dioxide is preferably in a range from 1 to 30% by weight, more preferably in a range from 2 to 20% by weight and further preferably in a range from 2 to 10% by weight relative to the amount of the composite particles.

If the amount of coating of the titanium dioxide particles is not sufficient, bioactivity deteriorates to result in the reduction in bonding ability with the bone. In addition, if the amount of the titanium dioxide particles for coating is too large, the titanium dioxide particles are likely to be left from the surface of the particles having radiopacity.

(Content Rate of Composite Particles)

The content rate of the composite particles is usually preferably 5% by weight or more and particularly preferably 10 to 30% by weight relative to the entirety of the bone cement composition in terms of bioactivity and radiopacity. In addition, the content rate is preferably 40% by weight or less in terms of the physical strength of the resulting hardened product of the bone cement composition. The content rate is appropriately set depending on applications for use, such as filling in a bone defective part, bonding of a prosthesis with its surrounding bones, and vertebroplasty.

(Base Material Formation Component: Methacrylate Polymer)

The methacrylate polymer constituting the base material formation component of the bone cement composition is one obtained by polymerizing a methacrylate monomer as a polymerizable monomer, and specific examples include (A) polyalkyl methacrylates such as polymethyl methacrylate (PMMA), polyethyl methacrylate (PEMA) and polybutyl methacrylate (PBMA), which are polymers of alkyl methacrylate monomers such as methyl methacrylate (MMA), ethyl methacrylate (EMA) and butyl methacrylate, (B) copolymers obtained by copolymerizing methyl methacrylate with at least one selected from the group consisting of styrene, ethyl methacrylate and methyl acrylate, and (C) polymers of dimethacrylate monomers such as bisphenol-A diglycidyl dimethacrylate (Bis-GMA), 2,2-bis[4-(3-methacryloxy-2-hydroxypropoxy)phenyl]propane, 2,2-bis(4-methacryloxyethoxyphenyl)propane(Bis-MEPP), triethylene glycol dimethacrylate (TEGDMA), diethylene glycol dimethacrylate (DEGDMA) and ethylene glycol dimethacrylate (EGDMA).

The weight average molecular weight of the methacrylate polymer is preferably 100,000 or more, further preferably 100,000 to 400,000 and particularly preferably 130,000 to 180,000.

The content rate of the methacrylate polymer is preferably 32.4 to 67.5% by weight relative to the entire of the bone cement composition.

The methacrylate polymer serving as the base material formation component can be obtained by mixing and kneading a methacrylate monomer serving as a component for base material formation and a polymerization initiator serving as a component for base material formation, and polymerizing the methacrylate monomer serving as a component for base material formation, as described later.

(Component for Base Material Formation: Methacrylate Monomer)

Specific examples of the methacrylate monomer include methyl methacrylate and ethyl methacrylate exemplified as the component to be polymerized for constituting the methacrylate polymer.

(Component for Base Material Formation: Polymerization Initiator)

Examples of the polymerization initiator include benzoyl peroxide, tert-butyl peroxide, lauroyl peroxide and azobisisobutyronitrile. Among them, benzoyl peroxide is preferable, and this benzoyl peroxide is used as the polymerization initiator to thereby provide the following advantage: a polymerization reaction is not only rapidly initiated but also easily continued.

(Optional Component as Component for Base Material Formation: Polymerization Accelerator)

The component for base material formation may include other optional components.

For example, for the purpose of allowing the polymerization reaction of the methacrylate monomer to further rapidly progress, a polymerization accelerator is preferably added together with the polymerization initiator. As the polymerization accelerator, for example, N,N-dimethyl-p-toluidine, tri-dimethylaminomethyl-phenol or the like can be used.

Among them, N,N-dimethyl-p-toluidine is preferably used because of being capable of allowing the polymerization reaction of the methacrylate monomer to rapidly progress.

(Optional Component as Component for Base Material Formation: Methacrylate Polymer)

In addition, in order to promote the polymerization reaction, a methacrylate polymer is preferably contained.

The methacrylate polymer includes those exemplified as the methacrylate polymer constituting the base material formation component, and may be used singly or in combination of two or more.

In addition, methacrylate polymers each having a different particle diameter may also be used as a mixture.

(Optional Components for Bone Cement Composition: Various Additives)

Furthermore, optional components such as various inorganic adding materials and organic adding materials may also be contained if necessary.

Examples of the inorganic adding material include calcium phosphates (hydroxyapatite and tricalcium phosphate), silicon oxide (silica) and aluminum oxide (alumina)

In addition thereto, for example, colouring agent, an antibiotic substance, an anticancer agent, a bone growth factor, and other pharmaceutically acceptable component may also be contained.

The content rate of such various additives can be appropriately set as long as the object of the present invention: the desired bioactivity and the desired radiopacity are achieved with the strength of the hardened product being maintained, is not imparted.

(Production of Bone Cement Composition)

The methacrylate monomer, the polymerization initiator and optional components as other components for base material formation are brought into contact with one another to thereby allow the polymerization reaction of the methacrylate monomer to progress, to result in a gradual increase in viscosity, thereby producing a pasty composition having an effective viscosity for filling in a bone defective part, bonding of an prosthesis to its surrounding bones, and use in vertebroplasty, namely, the bone cement composition of the present invention.

The polymerization reaction by contacting the methacrylate monomer with the polymerization initiator may be here performed in vitro, or the respective material components may be introduced to a portion that requires an artificial bone in vivo, and polymerized in situ. When the polymerization reaction is performed in vitro, the bone cement composition of the present invention is produced in advance, thereafter inserted to a high-releasable vessel having the desired shape before curing, and solidified for molding.

(Bone Cement Composition Kit)

The bone cement composition of the present invention can also be prepared by storing each of the material components for providing the bone cement composition in a separate storing parts as a kit in advance, and if necessary mixing kit components to thereby provide the bone cement composition, in term of easily production.

The storing parts may be any one as long as it can convey and store the kit component, and can be appropriately selected from vessels made of glass, metal, plastic, and the like, and packaging parts made of paper, plastic, and the like.

The bone cement composition kit of the present invention is for simply providing the bone cement composition of the present invention, finally, the hardened product of the bone cement composition which is the hardened product of the bone cement composition of the present invention In this bone cement composition kit of the present invention, the methacrylate monomer and polymerization initiator out of the composite particles, the methacrylate monomer and the polymerization initiator are components in the separate kit. That is to say, the kit has two kit components, a first component containing at least the polymerization initiator and a second component containing at least the methacrylate monomer. The composite particles is contained in the first component and/or the second component.

In the bone cement composition kit of the present invention, the polymerization initiator contained in the first component is usually solid, and the methacrylate monomer contained in the second component is usually liquid.

Since the composite particles are solid and have no reactivity with the polymerization initiator, the composite particles are preferably contained in the first component.

In addition, when the bone cement composition kit of the present invention includes the optional components, the optional components can also be each contained in a separate kit component, but are preferably contained in any of these two kit components in terms of convenience of conveyance and easiness of the polymerization reaction operation. Which kit component the optional components are contained in is appropriately selected depending on the reactivity with the material component contained in each of the first component and the second component and properties thereof.

For example, in the first component are contained solid material, one having reactivity with the methacrylate monomer, and methacrylate polymer fine particles that is usually solid, among the optional components. To the second component are added the polymerization accelerator that is usually liquid, and liquid one having no reactivity with the methacrylate monomer among the optional components.

(Method for Producing Bone Cement Composition)

The method for producing the bone cement composition of the present invention is a method for using the bone cement composition kit of the present invention to thereby provide a bone cement composition.

That is, a method is adopted which includes a step of mixing the first component and the second component constituting the bone cement composition kit of the present invention and polymerizing the methacrylate monomer in the presence of the composite particles. In this step, the first component and the second component are mixed and kneaded, for example, under ordinary pressure for 30 seconds, and thereafter further kneaded under a degassed atmosphere over 1 minute to thereby bring the methacrylate monomer into contact with the polymerization initiator, allowing the polymerization reaction of the methacrylate monomer to progress, thereby providing the bone cement composition of the present invention.

(Hardened Product of Bone Cement Composition)

Such a bone cement composition of the present invention is cured for a certain period of time to thereby form a hardened product of the bone cement composition, containing a base material made of the methacrylate polymer and the composite particles. The hardened product of the bone cement composition can be bonded to the bone in vivo by means of osteoconduction of titanium dioxide.

(Simulated Body Fluid)

Herein, the bioactivity can be usually evaluated by soaking the hardened product of the bone cement composition in a simulated body fluid. The simulated body fluid is an aqueous solution having the substantially same inorganic ion concentration as that of human plasma, and is one having a composition shown in Table 1 below. This simulated body fluid includes a simulated body fluid (SBF; Simulated Body Fluid) described in "T. Kokubo, H. Kushitani, S. Sakka, T. Kitsugi and T. Yamamuro, J. Biomed. Mater. Rer. 24, 721-734 (1990)".

TABLE 1

| Ion | Simulated body fluid (concentration/mM) | Blood (concentration/mM) |
|---|---|---|
| $Na^+$ | 142 | 142 |
| $K^+$ | 5.0 | 5.0 |
| $Mg^{2+}$ | 1.5 | 1.5 |
| $Ca^{2+}$ | 2.5 | 2.5 |
| $Cl^-$ | 148 | 103 |
| $HCO_3^-$ | 4.2 | 27.0 |
| $HPO_4^{2-}$ | 1.0 | 1.0 |
| $SO_4^{2-}$ | 0.5 | 0.5 |

Since the bone cement composition of the present invention contains a composite particle having a particle having radiopacity and a titanium dioxide coating with which the particle having radiopacity is coated, as a filler, the respective functions derived from the particle having radiopacity and the titanium dioxide coating are achieved, and also the resulting hardened product has a sufficient physical strength.

Furthermore, the bone cement composition of the present invention, while having the titanium dioxide coating present on only the surface of the particle in an extremely small amount, exhibits excellent bioactivity comparable with that exhibited by a bone cement composition using a titanium dioxide particle having a median diameter comparable with that of the composite particle.

According to the bone cement composition kit of the present invention, a kit component containing at least the first component and a kit component containing at least the second component can be simply mixed to thereby polymerize the methacrylate monomer in the presence of the composite particle, thereby easily producing the bone cement composition. Furthermore, the methacrylate monomer and the polymerization initiator can each be in a separate kit component to thereby prevent the methacrylate monomer from being polymerized in the state of being stored or conveyed before application.

In addition, when the bone cement composition kit of the present invention includes only two kit components of the first component and the second component, it is one having a small number of kit components and thus is superior in convenience of conveyance of the bone cement composition kit and polymerization reaction operation.

According to the method for producing the bone cement composition of the present invention, since the bone cement composition kit of the present invention is used, the kit components can be mixed to thereby easily form the bone cement composition of the present invention, as described above.

According to the hardened product of the bone cement composition of the present invention, bioactivity and physical strength suitable for use are achieved.

EXAMPLES

Hereinafter, specific Examples of the present invention will be described, but the present invention is not limited to these Examples.

In addition, the measurement method of the median diameter and the measurement method of the BET specific surface area performed in the following Examples and Comparative Examples are as follows.
(Measurement Method of Median Diameter)

The median diameter was measured by a laser diffraction/scattering-type particle size distribution analyzer, and as the laser diffraction/scattering-type particle size distribution analyzer, a particle size distribution measurement apparatus "LA-950" (manufactured by Horiba Ltd.) was used.

That is, powder particles to be measured for the median diameter were added to 50 ml of a dispersion medium made of an aqueous solution having sodium hexametaphosphate in a concentration of 0.2% by weight, and the resultant was stirred and mixed to thereby prepare a suspension. This suspension was charged from a sample inlet to a particle size distribution measurement apparatus "LA-950" (manufactured by Horiba Ltd.) and subjected to an ultrasonic dispersion for 3 minutes, and thereafter the measurement was started.
(Measurement Method of BET Specific Surface Area)

The BET specific surface area was measured by the nitrogen adsorption method, wherein the BET specific surface area measurement apparatus "MONOSORB" (manufactured by Quantachrome Instruments) was used.

This BET specific surface area measurement apparatus is for performing measurement by the BET single point method.
(Production Method 1 of Composite Particles: Preparation of Composite Particle A by Simultaneous Neutralization Method)
(1) Preparation of Barium Sulfate In a crucible was loaded 150 g of barium sulfate (median diameter: 0.3 μm, OC0413 purchased from Fushimi Pharmaceutical Co., Ltd.), calcined at 550° C. for 3 hours using an electric furnace (SK-3035F manufactured by Motoyama, the same shall apply hereinafter), and then subjected to dry pulverization, providing barium sulfate subjected to particle growth.

The median diameter of barium sulfate after calcining was 1.5 μm, the BET specific surface area thereof was 1.2 $m^2/g$, and the aspect ratio thereof was 1 to 1.6. The aspect ratio was calculated by drawing any straight line in a scanning electron micrograph (SEM), and measuring each of at least 6 particles present on the straight line to determine the average long diameter and the average short diameter.
(2) Production of Composite Particle A by Simultaneous Neutralization Method In a reaction vessel were mixed 20 g of the barium sulfate obtained in above (1) and 1000 ml of distilled water, and heated to 80° C. with stirring by a stirrer. Thereafter, 1.1 g of a 70% glycolic acid solution (purchased from Wako Pure Chemical Industries, Ltd.) was added, further 7% hydrochloric acid (purchased from Kanto Chemical Co., Inc.) was added thereto to adjust the pH to 2, and the resultant was stirred for 15 minutes.

Then, a solution having 35% hydrochloric acid (purchased from Wako Pure Chemical Industries, Ltd.) and 26.2 g of a titanium tetrachloride solution (glycolic acid/Ti molar ratio: 0.2) prepared so that the total amount was 1000 ml by pure water was dropped in the slurry of barium sulfate in 12 hours with the pH being kept at 2 by a 7.5% sodium hydroxide solution (purchased from Wako Pure Chemical Industries, Ltd.), and further kept for 6 hours. Then, the product was washed by filtration and thereafter dried at 100° C., subjected to dry pulverization, and thereafter calcined at 850° C. for 3 hours to thereby provide composite particle A.

The median diameter of composite particle A was 2.0 μm, and the BET specific surface area thereof was 2.4 $m^2/g$. It was confirmed by observation with a scanning electron microscope (S-3200N manufactured by Hitachi Ltd., the same shall apply hereinafter) that the surface of barium sulfate was coated with titanium dioxide without the titanium dioxide being ununiformly located. The scanning electron micrograph is shown in FIG. 1.

Figure 3:
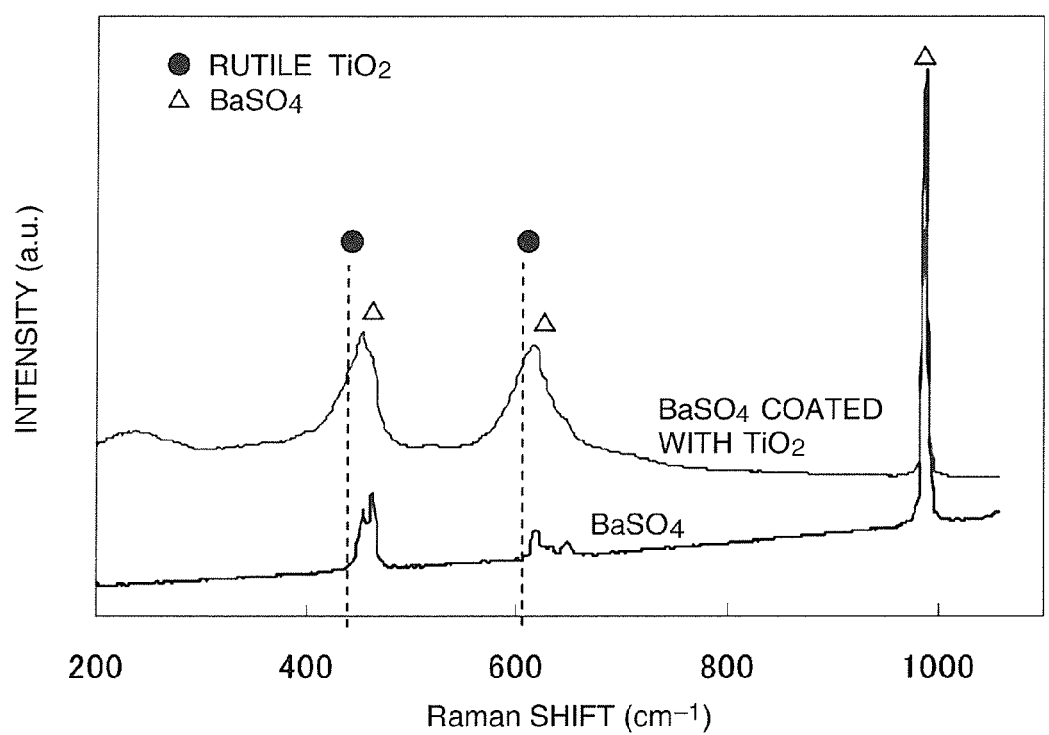
FIG. 3 is a Raman spectroscopic diagram of the composite particles obtained by a simultaneous neutralization method.

In addition, the measurement by a Raman spectrometry apparatus (JRS-SYSTEM2000 manufactured by RENISHAW, the same shall apply hereinafter) indicated that the titanium dioxide was present as rutile titanium dioxide (shown in FIG. 3), and the analysis by an X-ray fluorescence apparatus (XRF-1700 manufactured by Shimadzu Corporation, the same shall apply hereinafter) indicated that the composite particles contained titanium dioxide in 10% by weight.
(Production Method 2 of Composite Particles: Preparation of Composite Particle B by Spray Coating Method)

Figure 2:
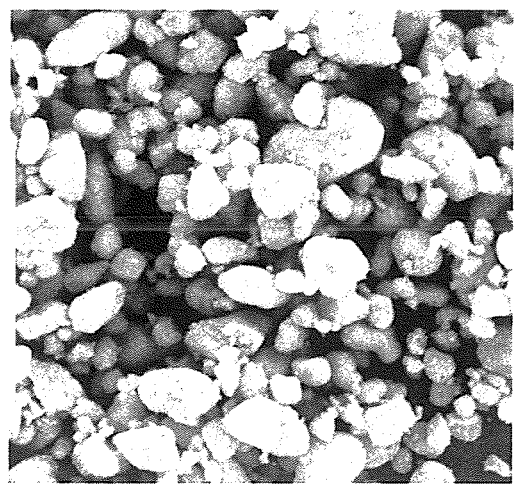
FIG. 2 is a scanning electron micrograph (SEM) of composite particles by a spray coating method.

In a Wurster fluid bed granulator (MP-01SPC, manufactured by Powrex Corp.) equipped with a forced circulation apparatus was loaded 1000 g of barium sulfate particles (median diameter: 2.5 μm) and convected in the apparatus, and thereafter 960 g of an aqueous titanium lactate complex solution ($TiO_2$: 2.9% by weight) was sprayed. Thereafter, 300 g of a slurry of rutile titanium dioxide fine particles ($TiO_2$: 10% by weight, produced by Ishihara Sangyo Kaisha, Ltd.) was subsequently sprayed. The charge air temperature and the exhaust temperature were kept at about 80 to 90° C. and about 40 to 50° C., respectively, in spraying, and production was made by a bottom spray at a flow rate of a spraying liquid of 4.0 to 6.0 g/min and an air volume charged of 1.0 to 1.2 $m^3$/min, providing composite particle B. The median diameter was 2.9 μm, and it was confirmed by observation with a scanning electron microscope that the surface of barium sulfate was coated with titanium dioxide. The scanning electron micrograph is shown in FIG. 2. In addition, the measurement by a Raman spectrometry apparatus indicated that the titanium dioxide was present as rutile titanium dioxide, and the analysis by an X-ray fluorescence apparatus (XRF-1700, manufactured by Shimadzu Corporation) indicated that the composite particles contained titanium dioxide in 6% by weight.

(Production Method 3 of Composite Particles: Preparation of Composite Particle C by Mechanical Dry-Treatment Method)

In a Henschel mixer (manufactured by Imoto Machinery Co., Ltd.) were loaded 550 g of barium sulfate particles (median diameter: 2.1 μm) and 11.5 g of rutile titanium dioxide (TTO-55N produced by Ishihara Sangyo Kaisha, Ltd., median diameter: 0.03 μm), and mixed at 1000 rpm for 5 minutes. Weighed were 510 g of mixed powders, and charged to a compression shearing-type dry powder composition apparatus "Nobilta" (NOB-130 manufactured by Hosokawa Micron), and the powders were treated at a load power of 3 kw for 30 minutes to provide composite particle C.

In addition, in order to fix the titanium dioxide subjected to coating, calcining was performed at 600° C. for 3 hours. The resulting particles calcined were treated by washing with hydrochloric acid, then washed by filtration with pure water, and subjected to a dry treatment at a temperature of 110° C. by using a constant temperature dryer. Thereafter, a dry pulverization treatment was performed by a centrifugal pulverizer "ZM1" in which a mesh having a screen diameter of 2 mm was set (manufactured by NISSEI Corporation) to thereby provide composite particle D.

Figure 6:
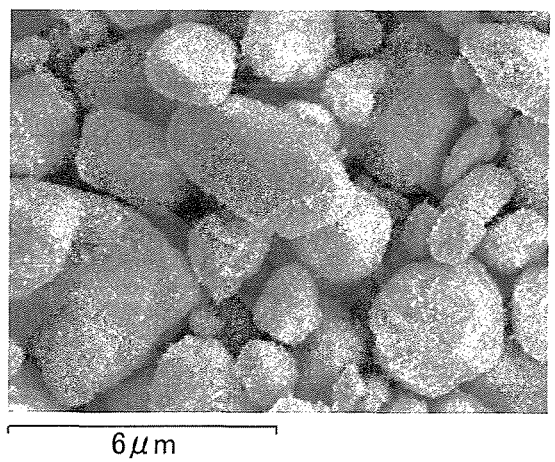
FIG. 6 is a scanning electron micrograph (SEM) of composite particle C by a mechanical dry-treatment method.
Figure 7:
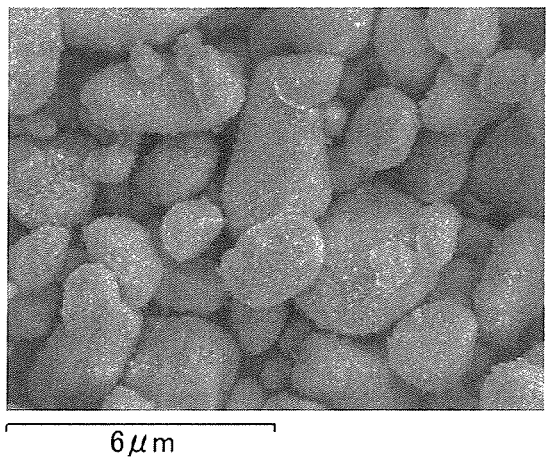
FIG. 7 is a scanning electron micrograph (SEM) of composite particle D by a mechanical dry-treatment method.
Figure 8:
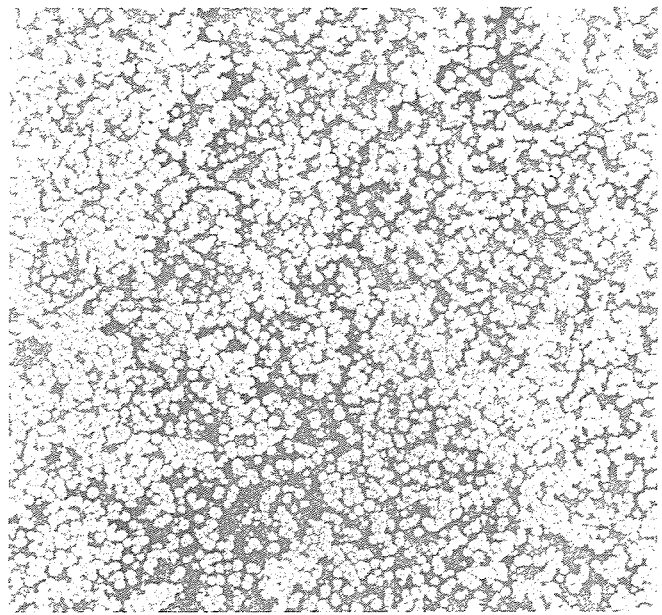
FIG. 8 are each a scanning electron micrograph (SEM) showing the surface of each hardened product in each of Examples 12 and 13, after soaking in a simulated body fluid.
Figure 8:
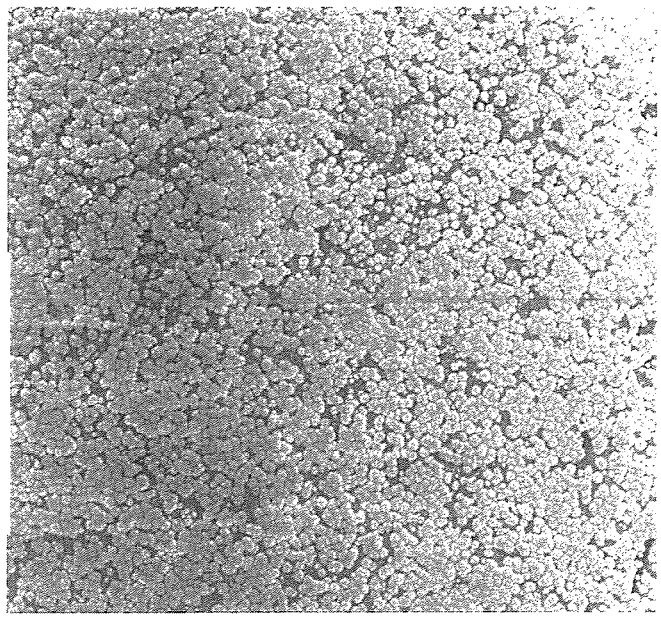

The median diameter of composite particle C was 2.1 μm, and the BET specific surface area thereof was 3.3 $m^2/g$. The median diameter of composite particle D was 2.1 μm, and the BET specific surface area thereof was 3.2 $m^2/g$. It was confirmed by observation with a scanning electron microscope (S-3200N, manufactured by Hitachi Ltd., the same shall apply hereinafter) that the surface of barium sulfate was coated with titanium dioxide without the titanium dioxide being ununiformly located. The scanning electron micrographs of composite particles C and D are shown in FIG. 6 and FIG. 7, respectively.

In addition, the measurement by a Raman spectrometry apparatus indicated that the titanium dioxide was present as rutile titanium dioxide, and the analysis by an X-ray fluorescence apparatus (XRF-1700, manufactured by Shimadzu Corporation) indicated that composite particle C and composite particle D contained titanium dioxide in 2% by weight and in 2% by weight, respectively.

Example 1

Composite particle A (2.10 g), 11.17 g of a polymethyl methacrylate/styrene copolymer powder (average particle diameter: 40 μm, average molecular weight: 150,000, particle shape: spherical shape, purchased from Sekisui Plastics Co., Ltd.), 1.89 g of polymethyl methacrylate fine particles (average particle diameter: 0.5 μm, average molecular weight: 300,000, particle shape: spherical shape, purchased from Sekisui Plastics Co., Ltd.) and 0.315 g of benzoyl peroxide (purchased from Sigma-Aldrich Co. LLC) were mixed using a Turbula shaker mixer (manufactured by Shinmaru Enterprises Corporation) over 10 minutes to thereby provide a mixed powder component.

On the other hand, 0.597 g of N,N-dimethyl-p-toluidine (purchased from Tokyo Chemical Industry Co., Ltd.) was added to 51.7 g of methyl methacrylate purchased from Sigma-Aldrich Co. LLC), and the resultant was mixed using a stirrer over 5 minutes to thereby provide a mixed liquid component.

Then, the mixed powder component and the mixed liquid component thus obtained were used to prepare a bone cement composition kit constituted by a first component composed of 14.81 g of the mixed powder component and a second component composed of 5.64 g of the mixed liquid component.

Then, in a kneading vessel made of polytetrafluoroethylene was loaded the first component (mixed powder component: 14.81 g) of the bone cement composition kit, thereafter charged the second component (mixed liquid component: 5.64 g) of the bone cement composition kit, and the resultant was kneaded under ordinary pressure over 30 seconds and then further kneaded under a degassed atmosphere over 1 minute to thereby provide a kneaded product (hereinafter, also referred to as "bone cement composition").

A preparation tool of a test piece for bioactivity, made of polytetrafluoroethylene, was loaded with the kneaded bone cement composition, capped, and left to still stand under an environment of a temperature of 23° C. for 40 hours or more for curing, and thus a disk-shaped hardened product of the bone cement composition, having a diameter of 15 mm and a thickness of 5 mm, was obtained.

In such a process in which the first component and the second component of the bone cement composition kit were mixed and kneaded to finally provide a hardened product of the bone cement composition, methyl methacrylate underwent a polymerization reaction to thereby form a base material made of the methacrylate polymer constituting the hardened product.

Examples 2 to 4 and Comparative Examples 1 to 10

The first component (mixed powder component) was changed as in Table 2 below to perform each of Examples 2 to 4 and Comparative Examples 1 to 10, providing each hardened product in each of Examples 2 to 4 and Comparative Examples 1 to 10. The procedure as in Example 1 was performed except that the first component was changed.

In Table, composite particle A is composite particle A by the simultaneous neutralization method shown in Production Method 1 of composite particles, and composite particle B is composite particle B by the spray coating method shown in Production Method 2 of composite particles.

In addition, the particles used in the spray coating method were used for $BaSO_4$ (median diameter: 2.5 μm), and those purchased from Ishihara Sangyo Kaisha, Ltd. were used for $TiO_2$ (median diameter: 4.0 μm).

TABLE 2

| | Composite particle | | | | Polymethyl methacrylate/ styrene | Polymethyl methacrylate | Benzoyl |
|---|---|---|---|---|---|---|---|
| | A | B | $BaSO_4$ | $TiO_2$ | copolymer | fine particles | peroxide |
| Example 1 | 2.10 | | | | 11.17 | 1.89 | 0.315 |
| Example 2 | 4.20 | | | | 9.38 | 1.59 | 0.315 |

TABLE 2-continued

| | Composite particle | | BaSO₄ | TiO₂ | Polymethyl methacrylate/ styrene copolymer | Polymethyl methacrylate fine particles | Benzoyl peroxide |
|---|---|---|---|---|---|---|---|
| | A | B | | | | | |
| Example 3 | 6.30 | | | | 7.58 | 1.29 | 0.315 |
| Example 4 | | 4.20 | | | 9.38 | 1.59 | 0.315 |
| Comparative Example 1 | | | 6.30 | | 7.58 | 1.29 | 0.315 |
| Comparative Example 2 | | | | 2.10 | 11.17 | 1.89 | 0.315 |
| Comparative Example 3 | | | | 4.20 | 9.38 | 1.59 | 0.315 |
| Comparative Example 4 | | | | 6.30 | 7.58 | 1.29 | 0.315 |
| Comparative Example 5 | | | 2.10 | 2.10 | 9.38 | 1.59 | 0.315 |
| Comparative Example 6 | | | 3.15 | 4.20 | 6.68 | 1.13 | 0.315 |
| Comparative Example 7 | | | 4.20 | 6.30 | 3.99 | 0.68 | 0.315 |
| Comparative Example 8 | | | 1.24 | 2.10 | 10.11 | 1.72 | 0.315 |
| Comparative Example 9 | | | 2.48 | 4.20 | 7.26 | 1.23 | 0.315 |
| Comparative Example 10 | | | 3.72 | 6.30 | 4.40 | 0.75 | 0.315 |

(Unit: g)

(Observation by Electron Microscope (Observation of Bioactivity))

Each of the hardened products prepared was soaked in a simulated body fluid (SBF; Simulated Body Fluid) under the condition of a temperature of 36.5° C. for 14 days, and thereafter the surface thereof was observed by a scanning electron microscope (SEM).

Figure 4:
FIG. 4 are each a scanning electron micrograph (SEM) showing the surface of each hardened product in each of Examples 1 to 3 and Comparative Example 1, after soaking in a simulated body fluid.
Figure 4:
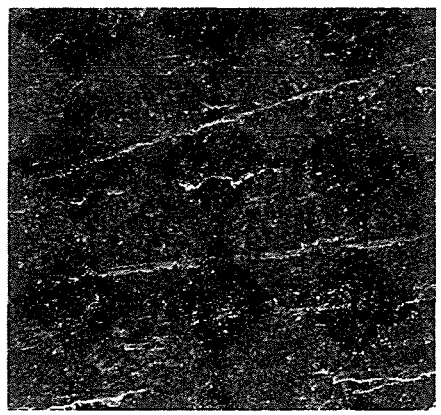
Figure 4:
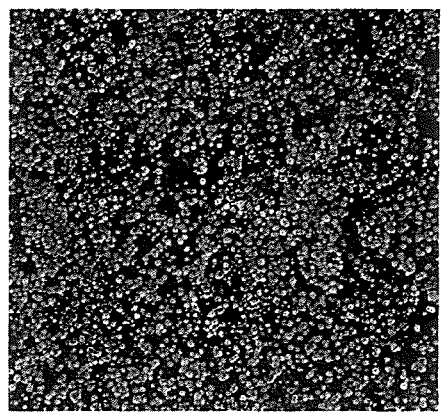
Figure 4:
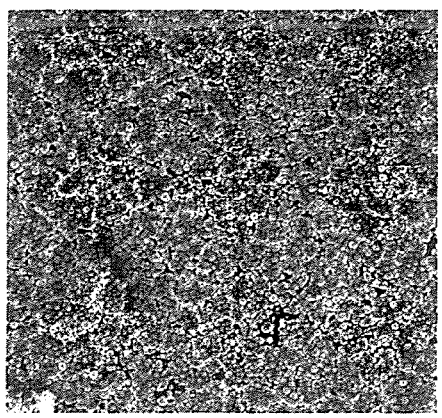

The results are shown in Table 3 below. Table 3, with respect to composite particles, barium sulfate and titanium dioxide, also shows the content rates thereof together. With respect to Examples 1 to 3 and Comparative Example 1, scanning electron micrographs (SEM) are also shown in FIG. 4.

TABLE 3

| | Composite particle | | BaSO₄ | TiO₂ | Bioactivity |
|---|---|---|---|---|---|
| | A | B | | | |
| Example 1 | 10 | | | | ++ |
| Example 2 | 20 | | | | ++ |
| Example 3 | 30 | | | | ++ |
| Example 4 | | 20 | | | + |
| Comparative Example 1 | | | 30 | | − |
| Comparative Example 2 | | | | 10 | ++ |
| Comparative Example 3 | | | | 20 | +++ |
| Comparative Example 4 | | | | 30 | +++ |
| Comparative Example 5 | | | 10 | 10 | ++ |
| Comparative Example 6 | | | 15 | 20 | ++ |
| Comparative Example 7 | | | 20 | 30 | ++ |
| Comparative Example 8 | | | 5.9 | 10 | ++ |
| Comparative Example 9 | | | 11.8 | 20 | ++ |

TABLE 3-continued

| | Composite particle | | BaSO₄ | TiO₂ | Bioactivity |
|---|---|---|---|---|---|
| | A | B | | | |
| Comparative Example 10 | | | 17.7 | 30 | ++ |

(Unit: % by weight)

In Table 3, the evaluation criteria of the bioactivity are as follows.

TABLE 4

| | HAp (hydroxyapatite) formation circumstance | Area of HAp on base plate |
|---|---|---|
| − | No HAp formation was observed | 0 |
| (±) | HAp was partially formed | 10% or less |
| ± | HAp was highly sparsely formed | up to 50% |
| + | HAp was formed all over base plate, but base plate was seen in spots | up to 80% |
| ++ | HAp was formed all over base plate, and base plate was hardly seen | up to 100% |
| +++ | HAp was formed all over base plate, and layered | 100% |

It was confirmed from the observation results by the electron microscope that good apatite formation was observed in the hardened product in each of Examples 1 to Example 4. It was confirmed that a high bioactivity was achieved in particular in the hardened product in each of Examples 1 to 3.

Example 5

Composite particle A (5.40 g) and 28.73 g of a polymethyl methacrylate/styrene copolymer powder (average particle diameter: 40 μm, average molecular weight: 150,000, particle shape: spherical shape; purchased from Sekisui Plastics Co., Ltd.) were mixed using a Henschel mixer (manufactured by Imoto Machinery Co., Ltd.) under the condition of a rotation number of 1,000 rpm over 5 minutes. Thereto were added 4.87 g of polymethyl methacrylate fine particles (average particle diameter: 0.5 μm, average molecular weight: 300,000, particle shape: spherical shape, purchased from Sekisui Plastics Co., Ltd.) and 0.810 g of benzoyl peroxide (purchased from Sigma-Aldrich Co. LLC), and the resultant was mixed using a Henschel mixer (manufactured by Imoto Machinery Co., Ltd.) under the condition of a rotation number of 1,000 rpm over 5 minutes to thereby provide a mixed powder component.

On the other hand, 0.156 g of N,N-dimethyl-p-toluidine (purchased from Tokyo Chemical Industry Co., Ltd.) was added to 14.413 g of methyl methacrylate (purchased from Sigma-Aldrich Co. LLC), and the resultant was mixed using a stirrer over 5 minutes to thereby provide a mixed liquid component.

Then, the mixed powder component and the mixed liquid component thus obtained were used to prepare a bone cement composition kit constituted by a first component composed of 39.81 g of the mixed powder component and a second component composed of 14.57 g of the mixed liquid component.

Then, in a kneading vessel made of polytetrafluoroethylene was loaded the first component (mixed powder component: 39.81 g) of the bone cement composition kit, thereafter charged the second component (mixed liquid component: 14.57 g) of the bone cement composition kit, and the resultant was kneaded under ordinary pressure over 30 seconds and then further kneaded under a degassed atmosphere over 1 minute to thereby provide a kneaded product (hereinafter, also referred to as "bone cement composition").

A preparation tool of a test piece for four-point bending strength, made of polytetrafluoroethylene, was loaded with the kneaded bone cement composition, capped, and left to still stand under an environment of a temperature of 23° C. for 40 hours or more for curing, and thus a plate-shaped hardened product having a width of 90 mm, a length of 90 mm and a thickness of 4 mm was obtained. This was cut to provide a hardened product of the bone cement composition, having a width of 10 mm, a length of 75 mm and a thickness of 3.3 mm (hereinafter, referred to as "hardened product").

In such a process in which the first component and the second component of the bone cement composition kit were mixed and kneaded to finally provide a hardened product of the bone cement composition, methyl methacrylate underwent a polymerization reaction to thereby form a base material made of the polymethacrylate polymer constituting the hardened product.

The first component and the second component were changed as shown in Table 5 below to perform each of Examples 6 to 8 and Comparative Examples 11 to 23, providing each hardened product in each of Examples 6 to 8 and Comparative Examples 11 to 23. The procedure as in Example 5 was performed except that the first component and the second component were changed.

In Table, composite particle A is composite particle A by the simultaneous neutralization method shown in Production Method 1 of composite particles.

In addition, the particles used in the spray coating method were used for BaSO₄ (median diameter: 2.5 μm), and those purchased from Ishihara Sangyo Kaisha, Ltd. were used for TiO₂ (median diameter: 4.0 μm).

TABLE 5

| | First component | | | | | | Second component | |
|---|---|---|---|---|---|---|---|---|
| | Composite particle A | $BaSO_4$ | $TiO_2$ | Polymethyl methacrylate/ styrene copolymer | Polymethyl methacrylate fine particles | Benzoyl peroxide | Methyl methacrylate | N,N-Dimethyl-p-toluidine |
| Example 5 | 5.40 | | | 28.73 | 4.87 | 0.810 | 14.413 | 0.156 |
| Example 6 | 10.80 | | | 24.11 | 4.09 | 0.810 | 14.413 | 0.156 |
| Example 7 | 17.10 | | | 20.58 | 3.49 | 0.855 | 15.344 | 0.165 |
| Example 8 | 24.20 | | | 16.67 | 2.83 | 0.908 | 16.273 | 0.176 |
| Comparative Example 11 | | 5.40 | | 28.73 | 4.87 | 0.810 | 14.413 | 0.156 |
| Comparative Example 12 | | 10.80 | | 24.11 | 4.09 | 0.810 | 14.413 | 0.156 |
| Comparative Example 13 | | 17.10 | | 20.58 | 3.49 | 0.855 | 15.344 | 0.165 |
| Comparative Example 14 | | 24.20 | | 16.67 | 2.83 | 0.908 | 16.273 | 0.176 |
| Comparative Example 15 | | | 5.40 | 28.73 | 4.87 | 0.810 | 14.413 | 0.156 |
| Comparative Example 16 | | | 10.80 | 24.11 | 4.09 | 0.810 | 14.413 | 0.156 |
| Comparative Example 17 | | | 17.10 | 20.58 | 3.49 | 0.855 | 15.344 | 0.165 |
| Comparative Example 18 | | | 24.20 | 16.67 | 2.83 | 0.908 | 16.273 | 0.176 |
| Comparative Example 19 | | 5.40 | 5.40 | 24.11 | 4.09 | 0.810 | 14.41 | 0.156 |
| Comparative Example 20 | | 8.55 | 11.40 | 18.14 | 3.08 | 0.855 | 15.344 | 0.165 |
| Comparative Example 21 | 3.19 | 5.40 | | 26.01 | 4.41 | 0.810 | 14.413 | 0.156 |
| Comparative Example 22 | 6.73 | 11.40 | | 19.70 | 3.34 | 0.855 | 15.344 | 0.165 |
| Comparative Example 23 | 10.71 | 18.15 | | 12.69 | 2.15 | 0.908 | 16.273 | 0.176 |

(Unit: g)

(Measurement of Four-Point Bending Strength)

The hardened product in each of Example 5 to Example 8 and Comparative Examples 11 to 23 was placed in a strength tester, and the four-point bending strength was measured.

The results are shown in Table 6 below. Table 6, with respect to composite particles, barium sulfate and titanium dioxide, also shows the content rates thereof together.

TABLE 6

| | Composite particle A (wt %) | BaSO$_4$ (wt %) | TiO$_2$ (wt %) | Four-point bending strength (MPa) |
|---|---|---|---|---|
| Example 5 | 10 | | | 82.6 |
| Example 6 | 20 | | | 83.0 |
| Example 7 | 30 | | | 77.8 |
| Example 8 | 40 | | | 49.0 |
| Comparative Example 11 | | 10 | | 76.0 |
| Comparative Example 12 | | 20 | | 64.0 |
| Comparative Example 13 | | 30 | | 55.1 |
| Comparative Example 14 | | 40 | | 43.0 |
| Comparative Example 15 | | | 10 | 83.5 |
| Comparative Example 16 | | | 20 | 77.7 |
| Comparative Example 17 | | | 30 | 61.0 |
| Comparative Example 18 | | | 40 | 50.0 |
| Comparative Example 19 | | 10 | 10 | 74.9 |
| Comparative Example 20 | | 15 | 20 | 66.0 |
| Comparative Example 21 | | 5.9 | 10 | 77.5 |
| Comparative Example 22 | | 11.8 | 20 | 67.3 |
| Comparative Example 23 | | 17.7 | 30 | 55.0 |

The hardened product in each of Examples 5 to 8 exhibited an excellent or comparable four-point bending strength as compared with the hardened product including a filler in a comparable amount in each of Comparative Examples 11 to 23.

Example 9

Composite particle A (2.10 g), 11.17 g of a polymethyl methacrylate/styrene copolymer powder (average particle diameter: 40 μm, average molecular weight: 150,000, particle shape: spherical shape, purchased from Sekisui Plastics Co., Ltd.), 1.89 g of polymethyl methacrylate fine particles (average particle diameter: 0.5 μm, average molecular weight: 300,000, particle shape: spherical shape, purchased from Sekisui Plastics Co., Ltd.) and 0.315 g of benzoyl peroxide (purchased from Sigma-Aldrich Co. LLC) were mixed using a Turbula shaker mixer (manufactured by Shinmaru Enterprises Corporation) over 10 minutes to thereby provide a mixed powder component.

On the other hand, 0.597 g of N,N-dimethyl-p-toluidine purchased from Tokyo Chemical Industry Co., Ltd.) was added to 51.7 g of methyl methacrylate purchased from Sigma-Aldrich Co. LLC), and the resultant was mixed using a stirrer over 5 minutes to thereby provide a mixed liquid component.

Then, the mixed powder component and the mixed liquid component thus obtained were used to prepare a bone cement composition kit constituted by a first component composed of 14.81 g of the mixed powder component and a second component composed of 5.64 g of the mixed liquid component.

Then, in a kneading vessel made of polytetrafluoroethylene was loaded the first component (mixed powder component: 14.81 g) of the bone cement composition kit, thereafter charged the second component (mixed liquid component: 5.64 g) of the bone cement composition kit, and the resultant was kneaded under ordinary pressure over 30 seconds and then further kneaded under a degassed atmosphere over 1 minute to thereby provide a kneaded product (hereinafter, also referred to as "bone cement composition").

A preparation tool of a test piece for bioactivity, made of polytetrafluoroethylene, was loaded with the kneaded bone cement composition, capped, and left to still stand under an environment of a temperature of 23° C. for 40 hours or more for curing, and thus a disk-shaped hardened product of the bone cement composition, having a diameter of 15 mm and a thickness of 5 mm, was obtained.

In such a process in which the first component and the second component of the bone cement composition kit were mixed and kneaded to finally provide a hardened product of the bone cement composition, methyl methacrylate underwent a polymerization reaction to thereby form a base material made of the methacrylate polymer constituting the hardened product.

Examples 10 to 11 and Comparative Examples 24 to 29

The first component (mixed powder component) was changed as in Table 7 below to perform each of Examples 10 to 11 and Comparative Examples 24 to 29, providing each hardened product in each of Examples 10 to 11 and Comparative Examples 24 to 29. The procedure as in Example 9 was performed except that the first component was changed.

In Table, composite particle A is composite particle A by the simultaneous neutralization method shown in Production Method 1 of composite particles, the particles used in the spray coating method were used for BaSO$_4$ (median diameter: 2.5 μm), and those purchased from Ishihara Sangyo Kaisha, Ltd. were used for TiO$_2$ (median diameter: 4.0 μm).

TABLE 7

| | Composite particle A | BaSO$_4$ | TiO$_2$ | Polymethyl methacrylate/ styrene copolymer | Polymethyl methacrylate fine particles | Benzoyl peroxide |
|---|---|---|---|---|---|---|
| Example 9 | 2.10 | | | 11.17 | 1.89 | 0.315 |
| Example 10 | 4.20 | | | 9.38 | 1.59 | 0.315 |
| Example 11 | 6.30 | | | 7.58 | 1.29 | 0.315 |
| Comparative Example 24 | | 2.10 | | 11.17 | 1.89 | 0.315 |

TABLE 7-continued

|  | Composite particle A | BaSO$_4$ | TiO$_2$ | Polymethyl methacrylate/ styrene copolymer | Polymethyl methacrylate fine particles | Benzoyl peroxide |
|---|---|---|---|---|---|---|
| Comparative Example 25 |  | 4.20 |  | 9.38 | 1.59 | 0.315 |
| Comparative Example 26 |  | 6.30 |  | 7.58 | 1.29 | 0.315 |
| Comparative Example 27 |  |  | 2.10 | 11.17 | 1.89 | 0.315 |
| Comparative Example 28 |  |  | 4.20 | 9.38 | 1.59 | 0.315 |
| Comparative Example 29 |  |  | 6.30 | 7.58 | 1.29 | 0.315 |

(Observation of Radiopacity)

Each of the hardened products prepared (test piece having a diameter of 15 mm and a thickness of 5 mm) was photographed using an X-ray apparatus for exclusive use of small animals VPX-40B (manufactured by Toshiba Medical Supply Co., Ltd.) under the conditions of a tube voltage of 42 kV and a photographing current-time product of 1.60 mAs. A Medical Film SRD (manufactured by Konica Minolta, Inc.) subjected to photographing was developed using an automatic developer AP500 (manufactured by Daito). As a result, the substantially same contrast property was observed in the test piece made of only barium sulfate and the test piece made of barium sulfate, having a titanium dioxide coating.

Figure 5:
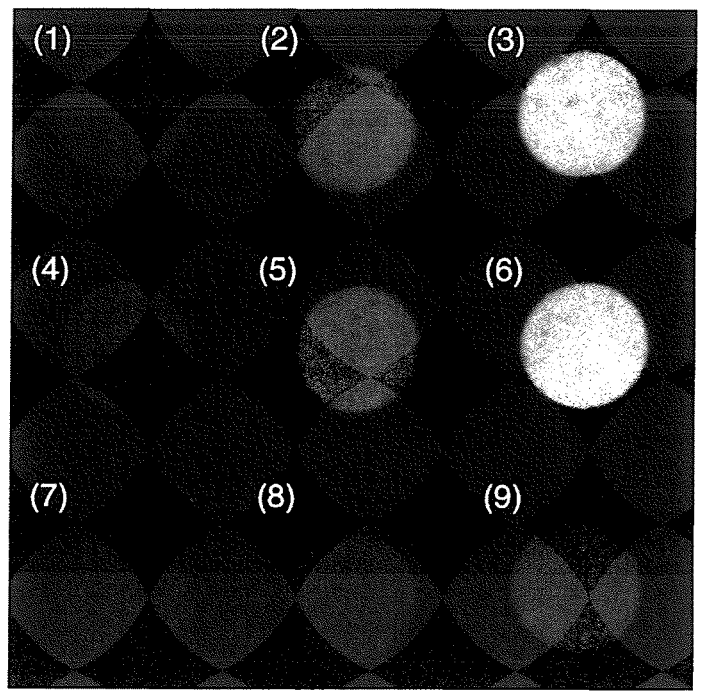
FIG. 5 are each an X-ray diagram showing the radiopacity of each hardened product in each of Examples 9 to 11 and Comparative Examples 24 to 29.

The X-ray contrast diagrams are shown in FIGS. 5. FIGS. 5(1) to (9) are as shown in Table 8 below. Table 8, with respect to composite particles, barium sulfate and titanium dioxide, also shows the content rates thereof together.

TABLE 8

|  | Composite particle A (wt %) | BaSO$_4$ (wt %) | TiO$_2$ (wt %) | FIG. 5 |
|---|---|---|---|---|
| Example 9 | 10 |  |  | (1) |
| Example 10 | 20 |  |  | (2) |
| Example 11 | 30 |  |  | (3) |
| Comparative Example 24 |  | 10 |  | (4) |
| Comparative Example 25 |  | 20 |  | (5) |
| Comparative Example 26 |  | 30 |  | (6) |
| Comparative Example 27 |  |  | 10 | (7) |
| Comparative Example 28 |  |  | 20 | (8) |
| Comparative Example 29 |  |  | 30 | (9) |

The test piece of the invention of the present application, including composite particles (barium sulfate coated with titanium dioxide) in each of Examples 9 to 11 of the present application, was coated with titanium dioxide, and therefore exhibited a contrast property substantially comparable with that exhibited by the test piece including barium sulfate in each of Comparative Examples 24 to 26, although having a smaller amount of barium sulfate by the amount of coating of titanium dioxide.

As is clear from the results in Table 3, Table 6 and Table 8, the bone cement composition comprising (a) a composite particle comprising a particle having radiopacity and a titanium dioxide coating with which the particle having radiopacity is coated, and (b) a base material formation component comprising a polymethacrylate polymer, of the invention of the present application, has achieved excellent results with respect to the bioactivity, four-point bending strength and contrast property all.

Example 12

Composite particle C (2.10 g), 11.17 g of a polymethyl methacrylate/styrene copolymer powder (average particle diameter: 40 μm, average molecular weight: 150,000, particle shape: spherical shape, purchased from Sekisui Plastics Co., Ltd.), 1.89 g of polymethyl methacrylate fine particles (average particle diameter: 0.5 μm, average molecular weight: 300,000, particle shape: spherical shape, purchased from Sekisui Plastics Co., Ltd.) and 0.32 g of benzoyl peroxide (purchased from Nacalai Tesque, Inc.) were mixed using a Turbula shaker mixer (manufactured by Shinmaru Enterprises Corporation) over 10 minutes to thereby provide a mixed powder component.

On the other hand, methyl methacrylate (purchased from Mitsubishi Gas Chemical Company, Inc.) and N,N-dimethyl-p-toluidine (purchased from Tokyo Chemical Industry Co., Ltd.) were weighed so that a ratio of 98.93% by weight:1.07% by weight was obtained, and the resultant was mixed using a stirrer over 5 minutes to thereby provide a mixed liquid component.

Then, the mixed powder component and the mixed liquid component thus obtained were used to prepare a bone cement composition kit constituted by a first component composed of 14.81 g of the mixed powder component and a second component composed of 5.64 g of the mixed liquid component.

Then, in a kneading vessel made of polytetrafluoroethylene was loaded the first component (mixed powder component: 14.81 g) of the bone cement composition kit, thereafter charged the second component (mixed liquid component: 5.64 g) of the bone cement composition kit, and the resultant was kneaded under ordinary pressure over 30 seconds and then further kneaded under a degassed atmosphere over 1 minute to thereby provide a kneaded product (hereinafter, also referred to as "bone cement composition").

A preparation tool of a test piece for bioactivity, made of polytetrafluoroethylene, was loaded with the kneaded bone cement composition, capped, and left to still stand under an environment of a temperature of 23° C. for 40 hours or more for curing, and thus a disk-shaped hardened product of the bone cement composition, having a diameter of 15 mm and a thickness of 5 mm, was obtained.

In such a process in which the first component and the second component of the bone cement composition kit were mixed and kneaded to finally provide a hardened product of the bone cement composition, methyl methacrylate underwent a polymerization reaction to thereby form a base material made of the methacrylate polymer constituting the hardened product.

Example 13

The first component (mixed powder component) was changed as in Table 9 below to perform Example 13, providing a hardened product in Example 13. The procedure as in Example 12 was performed except that the first component was changed.

In Table, composite particle C is composite particle C by the mechanical dry-treatment method shown in Production Method 3 of composite particles.

TABLE 9

| | Composite particle C | Polymethyl methacrylate/ styrene copolymer | Polymethyl methacrylate fine particles | Benzoyl peroxide |
|---|---|---|---|---|
| Example 12 | 2.10 | 11.17 | 1.89 | 0.32 |
| Example 13 | 4.20 | 9.38 | 1.59 | 0.32 |

(Unit: g)

(Observation by Electron Microscope (Observation of Bioactivity))

Each of the hardened products prepared was soaked in a simulated body fluid (SBF; Simulated Body Fluid) under the condition of a temperature of 36.5° C. for 14 days, and thereafter the surface thereof was observed by a scanning electron microscope (SEM).

The results are shown in Table 10 below. Table 10 also shows the content rate of composite particle C together. The evaluation criteria of the bioactivity in Table 10 are as shown in Table 4. The scanning electron micrograph (SEM) in Examples 12 and 13 was shown in FIG. 6.

TABLE 10

| | Content of composite particle (wt %) | Bioactivity |
|---|---|---|
| Example 12 | 10 | ++ |
| Example 13 | 20 | ++ |

It was confirmed from the observation results by the electron microscope that good apatite formation was observed and a high bioactivity was achieved in the hardened product in each of Examples 12 and 13.

Example 14

Composite particle C (14.20 g) and 75.55 g of a polymethyl methacrylate/styrene copolymer powder (average particle diameter: 40 μm, average molecular weight: 150,000, particle shape: spherical shape; purchased from Sekisui Plastics Co., Ltd.) were mixed using a Henschel mixer (manufactured by Imoto Machinery Co., Ltd.) at a rotation number of 1,000 rpm over 5 minutes. Thereto were added 12.81 g of polymethyl methacrylate fine particles (average particle diameter: 0.5 μm, average molecular weight: 300,000, particle shape: spherical shape, purchased from Sekisui Plastics Co., Ltd.) and 2.13 g of benzoyl peroxide (purchased from Sigma-Aldrich Co. LLC), and the resultant was mixed using a Henschel mixer (manufactured by Imoto Machinery Co., Ltd.) at a rotation number of 1,000 rpm over 5 minutes to thereby provide a mixed powder component.

On the other hand, 0.426 g of N,N-dimethyl-p-toluidine purchased from Tokyo Chemical Industry Co., Ltd.) was added to 39.43 g of methyl methacrylate (purchased from Sigma-Aldrich Co. LLC), and the resultant was mixed using a stirrer over 5 minutes to thereby provide a mixed liquid component.

Then, the mixed powder component and the mixed liquid component thus obtained were used to prepare a bone cement composition kit constituted by a first component composed of 41.97 g of the mixed powder component and a second component composed of 15.98 g of the mixed liquid component.

Then, in a kneading vessel made of polytetrafluoroethylene was loaded the first component (mixed powder component: 41.97 g) of the bone cement composition kit, thereafter charged the second component (mixed liquid component: 15.98 g) of the bone cement composition kit, and the resultant was kneaded under ordinary pressure over 30 seconds and then further kneaded under a degassed atmosphere over 1 minute to thereby provide a kneaded product (hereinafter, also referred to as "bone cement composition").

A preparation tool of a test piece for four-point bending strength, made of polytetrafluoroethylene, was loaded with the kneaded bone cement composition, capped, and left to still stand under an environment of a temperature of 23° C. for 40 hours or more for curing, and thus a plate-shaped hardened product having a width of 90 mm, a length of 90 mm and a thickness of 4 mm was obtained. This plate-shaped hardened product was cut to provide a hardened product of the bone cement composition, having a width of 10 mm, a length of 75 mm and a thickness of 3.3 mm (hereinafter, referred to as "hardened product").

In such a process in which the first component and the second component of the bone cement composition kit were mixed and kneaded to finally provide a hardened product of the bone cement composition, methyl methacrylate underwent a polymerization reaction to thereby form a base material made of the polymethacrylate polymer constituting hardened product (1).

Examples 15 and 16

The first component and the second component were changed as shown in Table 11 below to perform each of Examples 15 and 16, providing each hardened product in each of Examples 15 and 16. The procedure as in Example 14 was performed except that the first component and the second component were changed. In Table, composite particle C is composite particle C by the mechanical dry-treatment method shown in Production Method 3 of composite particles.

(Measurement of Four-Point Bending Strength)

The hardened product in each of Examples 14 to 16 was placed in a strength tester, and the four-point bending strength was measured. The results are shown in Table 11 below. Table 11 also shows the content rate of composite particle C together.

TABLE 11

| | Content of composite particle C (wt %) | First component | | | | Second component | | Four-point bending strength (MPa) |
|---|---|---|---|---|---|---|---|---|
| | | Composite particle C | Polymethyl methacrylate/ styrene copolymer | Polymethyl methacrylate fine particles | Benzoyl peroxide | Methyl methacrylate | N,N-Dimethyl-p-toluidine | |
| Example 14 | 10 | 14.20 | 75.55 | 12.81 | 2.13 | 39.43 | 0.426 | 79.1 |
| Example 15 | 20 | 28.40 | 63.41 | 10.75 | 2.13 | 39.43 | 0.426 | 68.7 |
| Example 16 | 30 | 43.80 | 52.72 | 8.94 | 2.19 | 40.54 | 0.438 | 56.0 |

The hardened product in each of Examples 14 to 16 exhibited an excellent or comparable four-point bending strength as compared with the hardened product including a filler in a comparable amount in each of Comparative Examples 11 to 23.

Example 17

Composite particle C (2.10 g), 11.17 g of a polymethyl methacrylate/styrene copolymer powder (average particle diameter: 40 μm, average molecular weight: 150,000, particle shape: spherical shape, purchased from Sekisui Plastics Co., Ltd.), 1.89 g of polymethyl methacrylate fine particles (average particle diameter: 0.5 μm, average molecular weight: 300,000, particle shape: spherical shape, purchased from Sekisui Plastics Co., Ltd.) and 0.315 g of benzoyl peroxide (purchased from Sigma-Aldrich Co. LLC) were mixed using a Turbula shaker mixer (manufactured by Shinmaru Enterprises Corporation) over 10 minutes to thereby provide a mixed powder component.

On the other hand, methyl methacrylate (purchased from Sigma-Aldrich Co. LLC) and N,N-dimethyl-p-toluidine (purchased from Tokyo Chemical Industry Co., Ltd.) were weighed so that a ratio of 98.93% by weight:1.07% by weight was obtained, and the resultant was mixed using a stirrer over 5 minutes to thereby provide a mixed liquid component.

Then, the mixed powder component and the mixed liquid component thus obtained were used to prepare a bone cement composition kit constituted by a first component composed of 14.81 g of the mixed powder component and a second component composed of 5.64 g of the mixed liquid component.

Then, in a kneading vessel made of polytetrafluoroethylene was loaded the first component (mixed powder component: 14.81 g) of the bone cement composition kit, thereafter charged the second component (mixed liquid component: 5.64 g) of the bone cement composition kit, and the resultant was kneaded under ordinary pressure over 30 seconds and then further kneaded under a degassed atmosphere over 1 minute to thereby provide a kneaded product (hereinafter, also referred to as "bone composition").

A preparation tool of a test piece for bioactivity, made of polytetrafluoroethylene, was loaded with the kneaded bone cement composition, capped, and left to still stand under an environment of a temperature of 23° C. for 40 hours or more for curing, and thus a disk-shaped hardened product of the bone cement composition, having a diameter of 15 mm and a thickness of 5 mm, was obtained.

In such a process in which the first component and the second component of the bone cement composition kit were mixed and kneaded to finally provide a hardened product of the bone cement composition, methyl methacrylate underwent a polymerization reaction to thereby form a base material made of the methacrylate polymer constituting the hardened product.

Examples 18 and 19

The first component (mixed powder component) was changed as in Table 12 below to perform each of Examples 18 and 19, providing each hardened product in each of Examples 18 and 19. The procedure as in Example 17 was performed except that the first component was changed. In Table, composite particle C is composite particle C by the mechanical dry-treatment method shown in Production Method 3 of composite particles.

(Observation of Radiopacity)

Each of the hardened products prepared (test piece having a diameter of 15 mm and a thickness of 5 mm) was photographed using an X-ray apparatus for exclusive use of small animals VPX-40B (manufactured by Toshiba Medical Supply Co., Ltd.) under the conditions of a tube voltage of 42 kV and a photographing current-time product of 1.60 mAs. A Medical Film SRD (manufactured by Konica Minolta, Inc.) subjected to photographing was developed using an automatic developer AP500 (manufactured by Daito). As a result, the substantially same contrast property was observed in the test piece made of only barium sulfate and the test piece made of barium sulfate, having a titanium dioxide coating.

Figure 9:
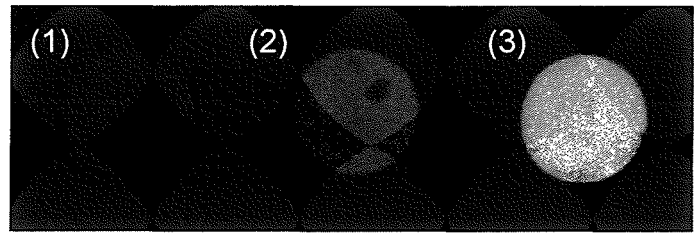
FIG. 9 are each an X-ray diagram showing the radiopacity of each hardened product in each of Examples 17 to 19.

The X-ray contrast diagrams are shown in FIGS. 9. FIGS. 9(1) to (3) are as shown in Table 12 below. Table 12 also shows the content rate of composite particle C together.

TABLE 12

| | First component | | | | | |
|---|---|---|---|---|---|---|
| | Content of composite particle C (wt %) | Composite particle C | Polymethyl methacrylate/ styrene copolymer | Polymethyl methacrylate fine particles | Benzoyl peroxide | FIG. 9 |
| Example 17 | 10 | 2.10 | 11.17 | 1.89 | 0.32 | (1) |
| Example 18 | 20 | 4.20 | 9.38 | 1.59 | 0.32 | (2) |
| Example 19 | 30 | 6.30 | 7.58 | 1.29 | 0.32 | (3) |

The test piece of the invention of the present application, including composite particles (barium sulfate coated with titanium dioxide) in each of Examples 17 to 19 of the present application, was coated with titanium dioxide, and therefore exhibited a contrast property substantially comparable with that exhibited by the test piece including barium sulfate in each of Comparative Examples 24 to 26 (FIGS. 5(4) to (6)), although having a smaller amount of barium sulfate by the amount of coating of titanium dioxide.

Example 20

Composite particle C (5.5 g), 8.88 g of a polymethyl methacrylate/styrene copolymer powder (average particle diameter: 40 μm, average molecular weight: 150,000, particle shape: spherical shape, purchased from Sekisui Plastics Co., Ltd.), 1.51 g of polymethyl methacrylate fine particles (average particle diameter: 0.5 μm, average molecular weight: 300,000, particle shape: spherical shape, purchased from Sekisui Plastics Co., Ltd.) and 0.33 g of benzoyl peroxide (purchased from Sigma-Aldrich Co. LLC) were mixed using a Turbula shaker mixer (manufactured by Shinmaru Enterprises Corporation) over 10 minutes to thereby provide a mixed powder component.

On the other hand, 0.206 g of N,N-dimethyl-p-toluidine (purchased from Tokyo Chemical Industry Co., Ltd.) was added to 19.0 g of methyl methacrylate (purchased from Sigma-Aldrich Co. LLC), and the resultant was mixed using a stirrer over 5 minutes to thereby provide a mixed liquid component.

Then, the mixed powder component and the mixed liquid component thus obtained were used to prepare a bone cement composition kit constituted by a first component composed of 4.94 g of the mixed powder component and a second component composed of 1.88 g of the mixed liquid component.

Then, in a kneading vessel made of polytetrafluoroethylene was loaded the first component (mixed powder component: 4.94 g) of the bone cement composition kit, thereafter charged the second component (mixed liquid component: 1.88 g) of the bone cement composition kit, and the resultant was kneaded under ordinary pressure for one minute and 30 seconds to thereby provide a kneaded product (hereinafter, also referred to as "bone cement composition").

A rat (Slc: Wistar lineage, 8-week old, male, Japan SLC, Inc.) under general anesthesia by intraperitoneal administration of pentobarbital sodium (Somnopentyl, Kyoritsuseiyaku Corporation) was subjected to the following surgery. The rat, hairs around both the knee joints being shaved, was secured on the surgical table in the supine position, and the surgical field was sterilized by ethanol. Skin incision of about 5 mm was performed in parallel with the tibia ridges inside. The periosteum was also incised in the same manner, and a bone groove having a length of 5 mm, reaching the bone-marrow space, was made using a drill. After the bone groove was washed well with saline, the bone cement composition kneaded was put into the bone-marrow space through the bone groove. After the absence of bleeding from the bone-marrow was checked, the subcutaneous tissue and the skin were sutured.

Example 21

The first component (mixed powder component) and the second component (mixed liquid component) were changed as shown in Table 13 below to perform Example 21. The procedure as in Example 20 was performed except that the first component was changed.

Comparative Example 30

Comparative Example 30 was performed according to the procedure as in Example 20 except that those in Comparative Example 3 were used as the first component (mixed powder component) and the second component (mixed liquid component).

TABLE 13

| | First component | | | | | Second component | |
|---|---|---|---|---|---|---|---|
| | Content of composite particle C (wt %) | Composite particle C | Polymethyl methacrylate/ styrene copolymer | Polymethyl methacrylate fine particles | Benzoyl peroxide | Methyl methacrylate | N,N-Dimethyl-p-toluidine |
| Example 20 | 25 | 5.5 | 8.88 | 1.51 | 0.33 | 19.0 | 0.206 |
| Example 21 | 30 | 6.6 | 7.94 | 1.35 | 0.33 | 19.0 | 0.206 |

(Unit: g)

(Evaluation of Bone Bonding Ability)

At 6 weeks after the surgery, the rat was euthanized, and the tibia was taken out. A microfocus X-ray CT system (SMX-100CT manufactured by Shimadzu Corporation) was used for tomography. The resulting image was used to perform image analysis, calculating the Affinity index. The Affinity index is a value represented by "%", the value obtained by dividing the length between the bone and the bone cement directly bonded thereto by the length of the periphery of the bone cement. The results are shown in Table 14.

TABLE 14

|  | Affinity index (%) |
| --- | --- |
| Example 20 | 65.1 ± 13.5 |
| Example 21 | 80.8 ± 6.43 |
| Comparative Example 30 | 66.3 ± 11.3 |

It was found from the evaluation results of the bone bonding ability that a bone bonding ability comparable with that in Comparative Example 30 was achieved in Example 20, and a bone bonding ability better than that in Comparative Example 30 was achieved in Example 21.

INDUSTRIAL APPLICABILITY

The bone cement composition using a composite particle in which a titanium dioxide coating is formed on a particle having radiopacity, of the invention of the present application, is suitably used for filling in a bone defective part, for bonding of a prosthesis to its surrounding bones, and for vertebroplasty. The bone cement composition of the invention of the present application can exert the desired bioactivity and the desired radiopacity while the strength of a hardened product is maintained.

The invention claimed is:

1. A bone cement composition comprising:
   (a) a composite particle comprising a particle having radiopacity and a titanium dioxide coating with which the particle having radiopacity is coated, and
   (b) a base material formation component comprising a methacrylate polymer.

2. The bone cement composition according to claim 1, wherein the particle having radiopacity has a granular shape.

3. The bone cement composition according to claim 1, wherein the composite particle has a median diameter of 0.2 to 7 µm.

4. The bone cement composition according to claim 1, wherein the composite particle has a BET specific surface area of 1 to 30 $m^2/g$.

5. The bone cement composition according to claim 1, wherein the titanium dioxide coating comprises rutile titanium dioxide.

6. The bone cement composition according to claim 1, wherein the composite particle further comprises a silica coating.

7. The bone cement composition according to claim 1, wherein the particle having radiopacity is made of barium sulfate or zirconium dioxide.

8. The bone cement composition according to claim 1, wherein the titanium dioxide coating comprises 1 to 30% by weight of the composite particle.

9. The bone cement composition according to claim 1, wherein the titanium dioxide coating comprises 2 to 20% by weight of the composite particle.

10. A bone cement composition kit comprising a first component comprising a polymerization initiator and a second component comprising a methacrylate monomer, wherein the first component and/or the second component comprise(s) a composite particle comprising a particle having radiopacity and a titanium dioxide coating with which the particle having radiopacity is coated.

11. A method for producing a bone cement composition, comprising the step of: polymerizing the methacrylate monomer according to the bone cement composition kit of claim 10.

12. A hardened product of the bone cement composition according to claim 1 or the bone cement composition produced by the method according to claim 11.

* * * * *